Figure 1:
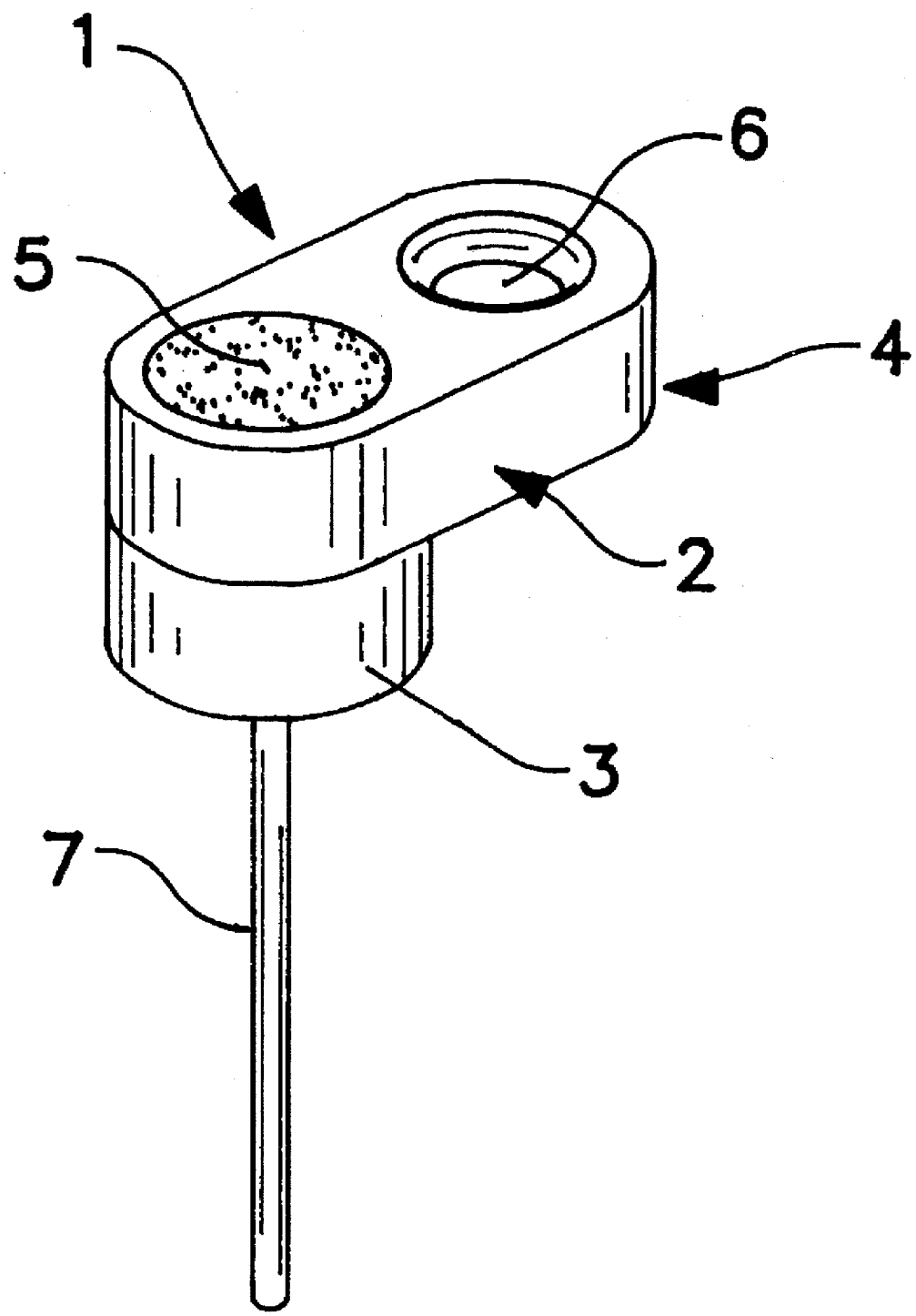

United States Patent [19]
Zenner et al.

[11] Patent Number: 5,895,372
[45] Date of Patent: *Apr. 20, 1999

[54] IMPLANTABLE DOSAGING SYSTEM

[76] Inventors: Hans Peter Zenner, Burgholzweg 149, D-72070 Tuebingen; Rolf Lehner, Bruehlstrasse 19, D-73734 Esslingen, both of Germany

[*] Notice: This patent issued on a continued prosecution application filed under 37 CFR 1.53(d), and is subject to the twenty year patent term provisions of 35 U.S.C. 154(a)(2).

[21] Appl. No.: 08/682,655

[22] PCT Filed: Jan. 26, 1995

[86] PCT No.: PCT/EP95/00280

§ 371 Date: Jul. 26, 1996

§ 102(e) Date: Jul. 26, 1996

[87] PCT Pub. No.: WO95/20409

PCT Pub. Date: Aug. 3, 1995

[30] Foreign Application Priority Data

Jan. 27, 1994 [DE] Germany ................... 44 02 380

[51] Int. Cl.⁶ .............................................. A61M 11/00
[52] U.S. Cl. .................. 604/93; 604/890.1; 604/152; 604/247
[58] Field of Search ........................ 604/890.1, 891.1, 604/152, 154, 247, 93

[56] References Cited

U.S. PATENT DOCUMENTS

| 4,013,074 | 3/1977 | Siposs ........................... 128/260 |
| 4,443,218 | 4/1984 | Decant, Jr. et al. ............. 604/67 |
| 4,936,831 | 6/1990 | Jaehrling et al. ............... 604/131 |
| 5,085,644 | 2/1992 | Watson et al. .................. 604/891.1 |

FOREIGN PATENT DOCUMENTS

| 0075762 | 4/1983 | European Pat. Off. . |
| 0142866 | 5/1985 | European Pat. Off. . |
| 0174757 | 3/1986 | European Pat. Off. . |
| 0258777 | 3/1988 | European Pat. Off. . |
| 0259668 | 3/1988 | European Pat. Off. . |
| 0335671 | 10/1989 | European Pat. Off. . |
| 0342945 | 11/1989 | European Pat. Off. . |
| 0342946 | 11/1989 | European Pat. Off. . |
| 0342947 | 11/1989 | European Pat. Off. . |
| 0450186 | 10/1991 | European Pat. Off. . |
| 3600217 | 9/1986 | Germany . |
| 3713061 | 11/1987 | Germany . |
| 3639980 | 5/1988 | Germany . |
| 3719238 | 12/1988 | Germany . |
| 3744527 | 7/1989 | Germany . |

(List continued on next page.)

OTHER PUBLICATIONS

Lynch, J: *Rückenmarksnahe Opiatanalgesie mit Pumpensystemen in der Tumorschmerztherapie*, Medizintechnik, 112. Jg., 1, 1992, pp. 22–27.

*Primary Examiner*—Michael Buiz
*Assistant Examiner*—Daphna Shaz
*Attorney, Agent, or Firm*—Eckert Seamans Cherin & Mellott, LLC

[57] ABSTRACT

An implantable dosaging system for medications, active substances, etc. administered in the form of dissolved or suspended fluids having a medication reservoir, a pump for administering the medication, an actuator for the transcutaneous operation of the pump, a self-sealing port, particularly for refilling the medication reservoir and optionally a dosaging line leading from the pump to the administration point of the medication. Preferably there is a housing (2) and a separate medication reservoir (9), in which the pump is located within the housing (2) and the administration of the medication takes place with the aid of a discharge opening provided in the housing (2), the actuator (5) and the self-sealing port (6) are provided on the housing (2), a connecting line (8) is provided between the housing (2) and the medication reservoir (9) and optionally the dosaging line (7) leads from the discharge opening to the administration point of the medication.

19 Claims, 6 Drawing Sheets

FOREIGN PATENT DOCUMENTS

| | | |
|---|---|---|
| 2916835 | 8/1990 | Germany . |
| 9107030 | 9/1991 | Germany . |
| 4038049 | 6/1992 | Germany . |
| 4038050 | 6/1992 | Germany . |
| 3321472 | 8/1992 | Germany . |
| 4123091 | 1/1993 | Germany . |
| 0878303 | 11/1981 | U.S.S.R. . |
| 0993954 | 2/1983 | U.S.S.R. . |
| 0993956 | 2/1983 | U.S.S.R. . |
| 1184542 | 10/1985 | U.S.S.R. . |
| 1225581 | 4/1986 | U.S.S.R. . |
| 87/04631 | 8/1987 | WIPO .................................. 604/891.1 |

IMPLANTABLE DOSAGING SYSTEM

The invention relates to an implantable dosaging system for medications, active substances, etc., which are in particular applied in the form of dissolved or suspended fluids.

Due to the fact that numerous medications act at different points of the body (ubiquitous), it is desirable to bring the said medications in a maximum targeted manner to the point or points of the organism where they are to have their intended action. In the case of systemic administration of medications acting in an ubiquitous manner, in part significant side effects can be observed. An oral administration of certain active substances is not always possible, because they are in part decomposed in the digestive tract. Thus, in many respects, there is a need to directly (intracorporal local) administer medications or active substances.

The local intracorporal administration is, however, complicated in numerous illnesses and complaints. If e.g. the medication is locally injected, said injection in almost each case must be given by trained therapists. This normally means that a doctor must be sought for each administration. In addition, most regions of the organism are difficultly accessible for a corresponding application and this more particularly applies to the skull region of the human. Thus, e.g. in certain treatments of the middle or inner ear a medication must be administered through the eardrum into the tympanic cavity. This is not only medically complicated, but also stressing for the patient.

The prior art discloses numerous implantable dosaging systems. According to DE 3639980 C1 a dosaging system comprises an implantable capsule, in which are located a medication collecting container and a pumping mechanism. An implantable catheter system with an injection port are provided for refilling the collecting container. The dosaging system is only suitable for rough dosaging purposes with individual doses of e.g. 2 ml.

EP 174 757 A1 describes a dosaging system in which the individual components such as the storage container, refilling point, pump and catheter are interconnected by connecting lines. The components are made from an elastomer. Such dosaging systems are difficult to implant due to the construction from numerous different parts.

EP 335 671 A1 discloses a dosaging system, in which the essential components are combined into a single structural unit. However, compared with the overall volume of the dosaging system, the size of the storage area in which the medication to be administered is located is small. In addition, the pumping mechanism provided has a complicated construction. The operability of the overall system is exclusively based on the elasticity of its components.

EP 342 945 A2, EP 342 946 A2 and EP 342 947 A2 disclose a very similar dosaging system to that described in EP 335 671 A1. Here again the pumping mechanism used is very complicated and the quantity of the medication which can be received in the storage space is small compared with the overall volume of the space taken up. Here again the operability of the dosaging system is based on the deformability of the housing containing the pumping mechanism and the actual pumping mechanism.

The problem of the invention is to avoid the disadvantages known from the prior art. Thus, in particular, a large storage space compared to the overall dimensions of the dosaging system is to be provided, so as to be able to perform a maximum number of individual administrations before the storage space has to be refilled. Simultaneously the construction of the pumping mechanism is to be made as simple as possible and therefore less prone to faults. Finally, by suitable measures, it is to be ensured that small, precisely defined active substance quantities are easily administered and the system can be refilled without great effort a number of times. In particular, a dosaging system according to the invention is to be suitable for an at least partial implantation in bones or bone cavities.

This problem is solved by a dosaging system of the aforementioned type, which has the following components:

a medication reservoir, a pump for administering the medication, an actuator for the transcutaneous actuation of the pump, a self-sealing port, particularly for refilling the medication reservoir and optionally a dosaging line leading from the pump to the medication administration point.

Preferred embodiments of the invention are described in the subclaims. The wording of all the claims is made by reference to part of the content of the description.

As a function of the intended use the indicated components can be combined into individual structural parts of the dosaging system. Thus, it is e.g. possible to provide a separate medication reservoir in the form of an elastic or rigid housing and to provide thereon the self-sealing port, particularly a septum. In such cases it is appropriate to place the pump within a further housing and to also provide the actuator for the transcutaneous actuation of the pump on said second housing. The medication reservoir with the self-sealing port and the second component with the pump and actuator are in such cases interconnected by means of a connecting line with the aid of which the medication to be administered is transferred from the medication reservoir into the second component. The transfer of the medication to the administration point then takes place by a dosaging line positioned on the second component.

In preferred embodiments of the invention there is a housing and a separate medication reservoir, wherein the pump is located within the housing, there is a discharge opening in the housing for administering the medication with the aid of the pump, the actuator and the self-sealing port are located on the housing, a connecting line is provided between the housing and the medication reservoir, and the optionally provided dosaging line leads from the discharge opening on the housing to the medication administration point.

Numerous advantages result from the dosaging system proposed by the invention and in particular the last-mentioned construction. There is a simple, compact construction of relatively few components, which are in turn simply constructable and designable. This not only leads to comparatively low costs when manufacturing the system, but also ensures a troublefree operation of the dosaging system when in use. The operation of the system can also not be negatively influenced by external influences such as e.g. vibrations, temperature, position and pressure changes. The dosaging system according to the invention is transcutaneously operable, particularly by the fingers of the patient. No trained personnel is needed for the individual administration. There is also no need for an energy storage device, such as e.g. a storage battery or button cell, or for an additional system such as a control unit or a remote control. Simultaneously the system can be transcutaneously cleaned, disinfected and refilled in the implanted state. The useful volume of the system for the medication to be administered is comparatively large compared with the space taken up by the overall system. This means that numerous individual administrations can take place before the medication reservoir has to be refilled. This advantage also manifests itself if e.g. there is a separate (interchanged) medication reservoir, which is to be implanted at another point in the organism to e.g. the component having the pump. In such cases the medication reservoir volume can be optionally further increased. By installing the dosaging system directly on or in the vicinity of the location where the medication or active substance is to act, there is a significant reduction to the described side effects occurring with ubiquitous acting medications.

Due to the dosaging line between the discharge opening of the pump and the medication administration point provided in the dosaging system according to the invention, it is ensured that administration can take place precisely at a preselected point of the organism.

The essential components of the dosaging system and in particular those coming into contact with the organism such as the housing, can be made from any random biocompatible material. Correspondingly the system can be used at any random point in the organism. Preference is given to a dosaging system in which a large part of the system components, particularly the housing containing the pump, are made up from a dimensionally stable, substantially rigid material having an adequate strength. This can be a corresponding plastics material, particularly polyurethane (PUR) or polysulphone (PSU) and/or a corresponding metal, particularly (pure) titanium. Compared with plastic titanium has a high strength and allows the use of thin-walled components. Its affinity to the bone tissue, optionally reinforced by a suitable surface treatment, aids the growing in of the housing into the bony implant member. Through using a rigid housing it is ensured that, optionally with the exception of parts of the actuator and an elastic, separate medication reservoir, no elastic, deformable parts are present. Thus, these embodiments are particularly suitable for use in the vicinity of bones, particularly the skull bone of the human. A dosaging system with a rigid (pump) housing can be housed with particular advantage in a corresponding bone recess and can, if necessary, be fixed there.

A separate medication reservoir preferably comprises an elastic and therefore deformable (biocompatible) material, particularly an elastic plastics material. The necessary elasticity can e.g. also be attained by a metal bellows. Such an elastic reservoir can optionally be located in a further, preferably rigid housing made from the aforementioned biocompatible materials. Separate medication reservoirs are conventionally also provided for implantation purposes, particularly under the skin by fixing (suturing) to the muscular fascia, preferably in the vicinity of the axilla, neck or occiput.

For optionally present, further elastic components (catheters, membranes) it is possible to use polymers such as silicones, polyurethanes (PUR) and Teflon (PTFE). Spring elastic parts, such as e.g. restoring springs, can be made from titanium or also high-alloyed, implantable special steels. Intrinsic system components, such as pump parts, e.g. valves, can also be made from titanium.

The housing present in the preferred embodiments can be formed in one piece. According to a further development, the housing preferably comprises a housing base part and a housing lid placed on said base part. The base part and lid can be connected in any random way, e.g. by screwing, bonding, welding, locking in of the lid, etc.

As has already been stated, the dosaging system according to the invention can be used anywhere in the organism, preferably in the vicinity of bones and bone cavities. As has already been indicated, the complete system can be installed at the selected point or this can only apply to part of the overall system, such as e.g. a housing with actuator, pump, optionally dosing line and optionally filling opening. A separate, in particular elastic medication reservoir with or without a filling opening is then implanted e.g. at another point in the organism and connected to the housing by means of a connecting line.

One possible use for the dosaging system according to the invention consists of bone parts of humans and animals located under the skin and which are sufficiently large for an implantation of the dosaging system or its corresponding parts. Such bone parts are e.g. encountered on the skull bone, its cavities or the pelvic bone of the human. Such a use has the advantage that the system in the case of corresponding installation cannot be seen from the outside and in this way there is a great reduction to a possible stigmatization of the patient. In preferred embodiments of the invention the housing shape is correspondingly constructed for an implantation in the human in the vicinity of the skull bone, particularly in the bone cavity area behind the ear muscle. This bone cavity area behind the ear muscle (mastoid) is a particularly good use point for the dosaging system for the treatment of the middle and inner ear, because it is naturally connected to the middle ear and via the membranes of the round and oval window also with the inner ear.

In the invention the housing preferably forms a first portion and a second portion immediately adjacent to the first portion within the housing. In this embodiment the pump is preferably provided in the housing part forming the first portion. The actuator for the pump is in particular then located on the first portion. Thus, the first portion can be formed by a substantially cylindrical part of the housing, in which the pump is vertically positioned (perpendicular to the top of the housing) and in which the actuator is located on the top of the cylinder and the discharge opening of the pump on the bottom of the cylinder. In a further development the self-sealing port is provided on the second portion of the system. As a result, it is inter alia achieved that the actuation of the pump and the refilling of the medication reservoir can take place at different points in the system.

A ventilation of the medication reservoir can either take place directly by means of a ventilation line or passively by means of a semipermeable membrane located in the housing, e.g. of porous PTFE or silicone. Although the latter allows air to enter the system (e.g. from the air-filled middle ear), keeps the medication in the reservoir in the opposite direction. Finally, the pressure compensation in the system (medication reservoir) can also take place by body fluid. The body fluid and medication a re separated by an elastic membrane or a barrier element displaceable or deformable by differential pressure. If a (separate) elastic medication reservoir (e.g. of silicone) is used, there is no need for a ventilation mechanism. The medication volume taken through pump application is compensated by the deformation of the reservoir geometry.

The actuator, e.g. an operating button, according to the invention preferably essentially comprises a pressure surface, which cooperates with the pump, e.g. the piston of a piston pump. This pressure surface can preferably have a substantially elastic cover membrane by means of which the fingers act on the pump, e.g. in transcutaneous actuation. The actuator, particularly the cover membrane, can have a slightly raised construction, i.e. at least partially raised compared with their environment, e.g. the housing lid. Thus, the actuating point can be more easily found by the patient and the operation of the dosaging system is further facilitated. The diameter of the actuator is appropriately adapted to the size of a finger used for actuation and is preferably approximately 10 to 20 mm. Preferably there is an automatic resetting of the actuator, e.g. by a spring function. The actuating force is preferably set so high that it is possible to exclude an unintended operation of the system (e.g. through head movements of the patient in sleep). However, it is advantageous for the actuating force not to be sufficiently high to enable tissue damage (pressure necrosis) to occur to the implant-covering tissue or implant member. The actuating stroke of the actuator is preferably between 1 and 2 mm. The actuating forces can in particular be 1 to 5 N (Newton), preferably 1 to 2 N.

In the case of the self-sealing port according to the invention, it enables the medication reservoir to e.g. be emptied, cleaned, disinfected, ventilated and refilled. Such a port is preferably formed by a suitable membrane such as e.g. a so-called puncture septum.

In these cases the medication reservoir is emptied or filled with the aid of special cannulas. By a corresponding choice of the puncture septum the process can be very frequently repeated. In a further development a centring radius can be provided on the port through which the membrane is positioned somewhat more deeply than the surface of the corresponding housing. This facilitates the finding of the port on the implanted housing and the puncturing of the special cannula. For easier detection of the port the surface of the membrane or also the point of the skin located above the port can be given a corresponding screen.

The size of the medication reservoir is substantially freely selectable as a function of the intended use. Volumes up to 10 $cm^3$ can be obtained, particularly when using a separate (elastic) medication reservoir. Appropriately, particularly when using the overall system in the vicinity of the mastoid, volumes are adopted between approximately 1 and 5 $cm^3$, particularly between approximately 1 and 2.5 $cm^3$, preferably between approximately 1 and 2 $cm^3$. As a result of these relatively large quantities with at the same time comparatively small dimensions of the overall system, it is relatively rarely necessary for the patient to refill the medication reservoir. Therefore, inter alia, personal treatment costs can be considerably lowered.

According to the invention, the pump is preferably provided for the discontinuous dosaging of quantities in the microlitre range (microdosaging system). In this way small, fixed settable quantities can be administered. Preferred dosages are between 1 and 100 µl and within this range between 5 and 10 µl and between 10 and 20 µl per actuation of the system.

It is possible in the invention to use all pump types, particularly non-rotary pumps. However, preference is given to a so-called piston pump, particularly a plunger pump or a so-called diaphragm pump. Preferably the pump according to the invention has a suction valve for the fluid, which in the case of an overpressure has a blocking action in the pump chamber and opens in the case of underpressure. In a further development preferably a pressure valve is provided for the fluid, which blocks in the case of an underpressure in the pump chamber and opens in the case of an overpressure. In preferred embodiments the suction valve and pressure valve operate alternately as a function of the hydrostatic pressure in the pump chamber.

Finally, preferably in the case of the pump is provided a ventilating valve serving as a ventilating mechanism. The ventilating valve opens automatically when there is a sufficiently high underpressure or vacuum in the medication reservoir and thus permits a pressure balance.

The system can also have an acoustic signal generator, which e.g. indicates the pump function. In this way the patient is acoustically informed that the pump has been actuated and the medication dosaged. In this case the signal generator is preferably fitted to the pump, e.g. being coupled to the piston stroke. A signal generation can also be provided for indicating the medication reservoir fill level, so that it is indicated to the patient in good time when the reservoir requires refilling. The medication reservoir filling level can also be ultrasonically indicated.

The dosaging line between the pump discharge opening and the medication administration point preferably has at one of its ends a closure valve, which is preferably provided on the line end associated with the administration point. This prevents a growing in of tissue and therefore a blockage of the line. For achieving the same objective additionally or alternatively the internal diameter of the dosaging line can be made as small as possible. As a result of this and further measures the dosaging line can be appropriately constructed for administering a therapeutic to the middle ear.

The invention also covers the use of the describe dosaging system in the preparation of a therapeutic. This use is in particular directed at the provision of a therapeutic for local therapy of the middle and inner ear. Preferably the inner ear undergoes therapy by applying a medication, active substance or the like to the middle ear. A corresponding use occurs more particularly in the treatment of tinnitus aureum, Ménière's disease, chronic middle ear inflammation and pain therapy in the skull region. The mastoid is particularly suitable for receiving the dosaging system or part thereof (particularly the housing with pump and port). Preferably fixing takes place in the bone region behind the ear muscle (mastoid) of the human. For fixing purposes it is possible to use suitable screws, e.g. titanium screws or special cements such as e.g. glass ionomer cement. It is also possible to bring about fixing with absorbable suture material and the growing of bone cells into the pores of the housing material (titanium).

For the implantation of the dosaging system provided by the invention, in this case the bone cavity region behind the ear muscle is correspondingly drilled out and the preferred form of the housing corresponds to the structure of the mastoid. Subsequently a connection is created or used in the tympanic cavity (aditus ad antrum or through the rear acoustic duct wall) through the dosaging line can be introduced into the tympanic cavity. Subsequently the dosaging system/housing is fixed in the cavity created. For simplifying implantation the inventive dosaging system can be made available in certain standardized sizes, which are adapted to the different sizes of the corresponding bone part behind the ear. An optionally provided, separate medication reservoir with or without a port can also be provided at another point, e.g. in the neck region, axilla region or on the back of the head. The dosaging line introduced into the opening can be fixed at virtually random locations in the middle ear in the case of middle and inner ear therapy, e.g. in the vicinity of the so-called round window, e.g. using special cements or a titanium clip. The active substance can diffuse through the round window membrane into the inner ear lymph. It is also possible to directly connect a dosaging line to the liquid of the inner ear or to the vestibular organ.

The described features and further features of the invention can be gathered from the following description of preferred embodiments in conjunction with the subclaims and drawings. The individual features can be implemented individually or in the form of combinations. In the drawings show:

FIG. 1. The diagrammatic overall view of a dosaging system according to the invention.

Figure 2:
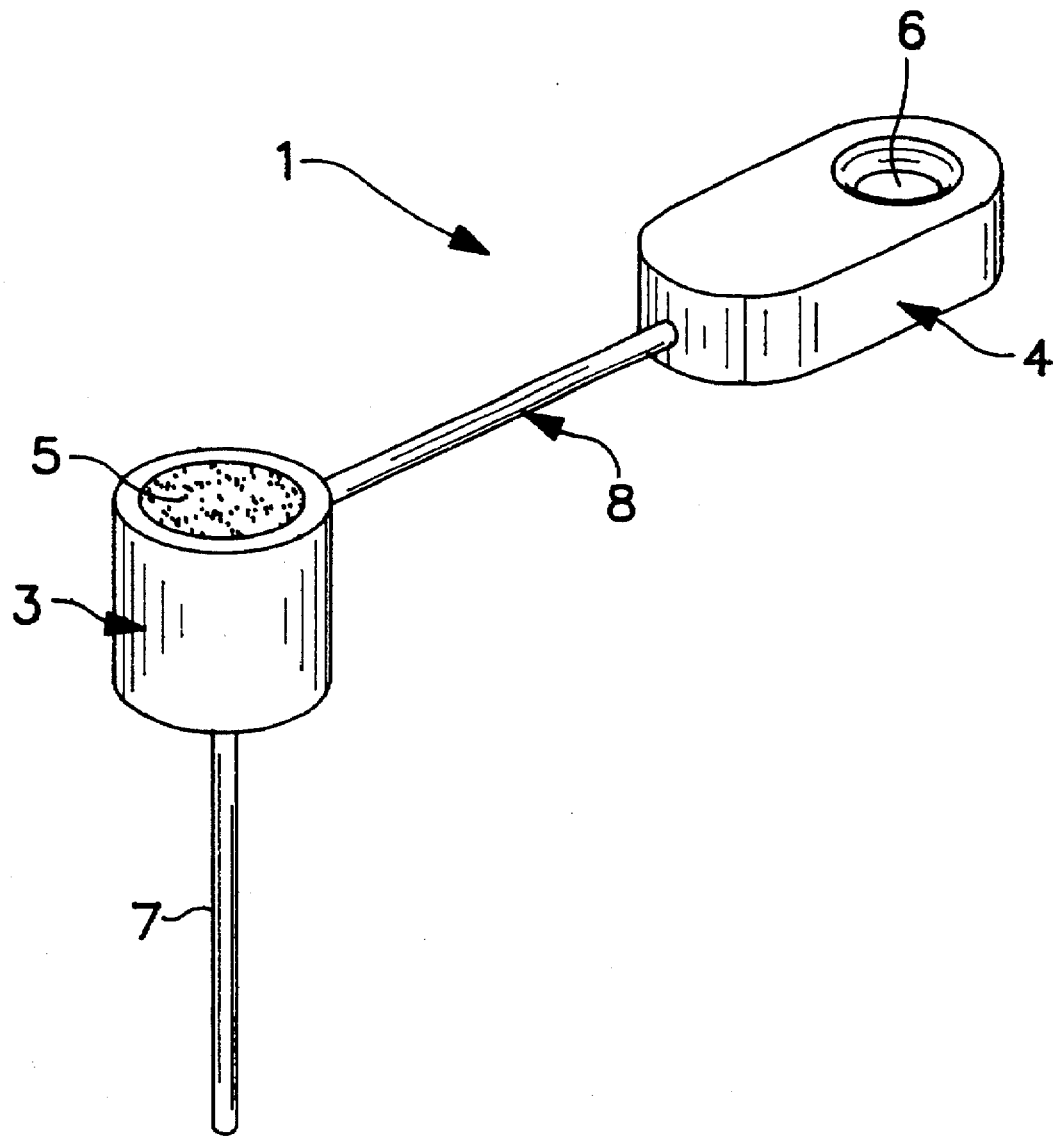

FIG. 2. The diagrammatic overall view of a second dosaging system according to the invention.

Figure 3:
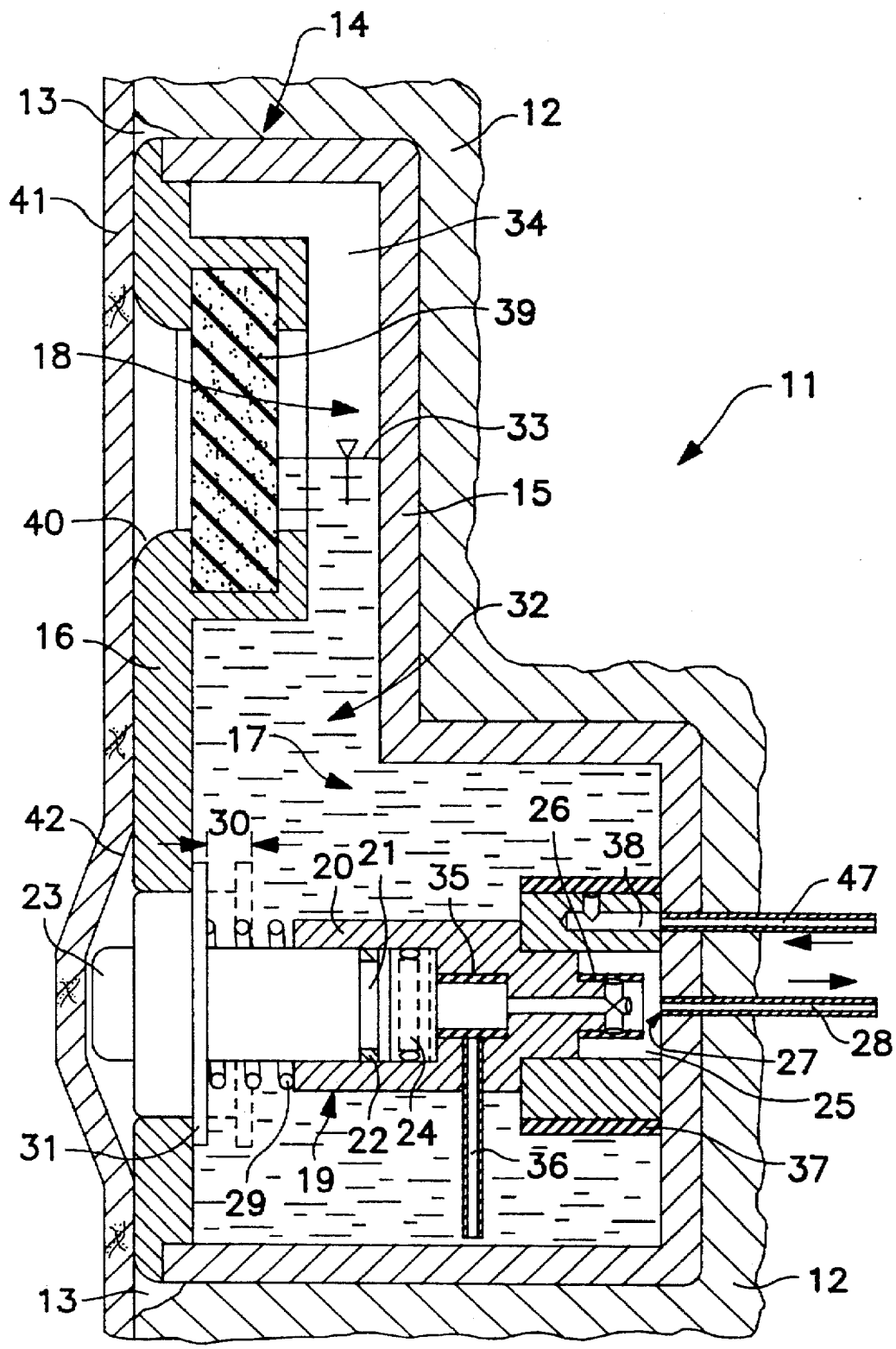

FIG. 3. The sectional view of a dosaging system according to FIG. 1 having a piston pump in the implanted state.

Figure 4:
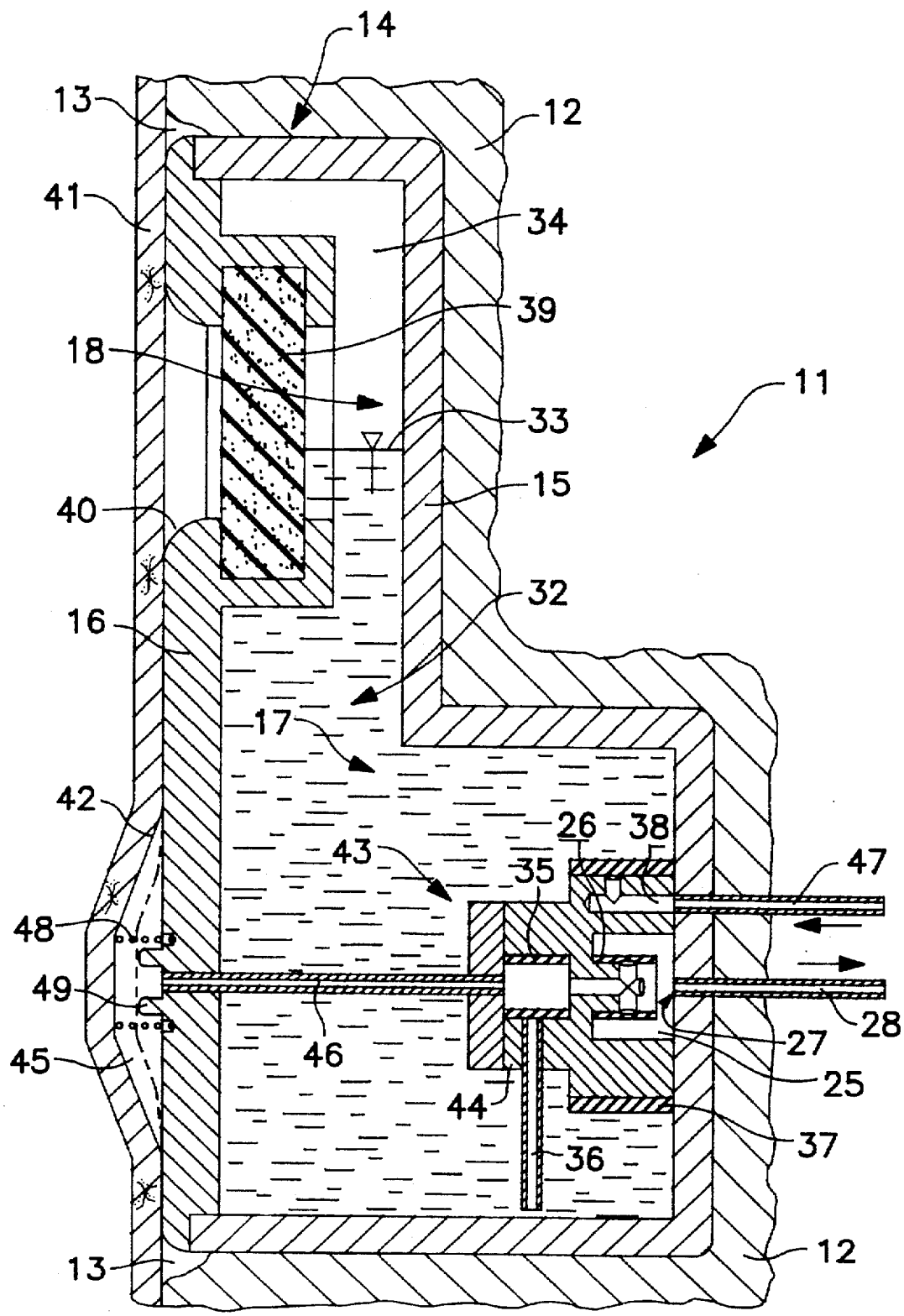

FIG. 4. The sectional view of an inventive dosaging system according to FIG. 1 with a diaphragm pump in the implanted state.

Figure 5:
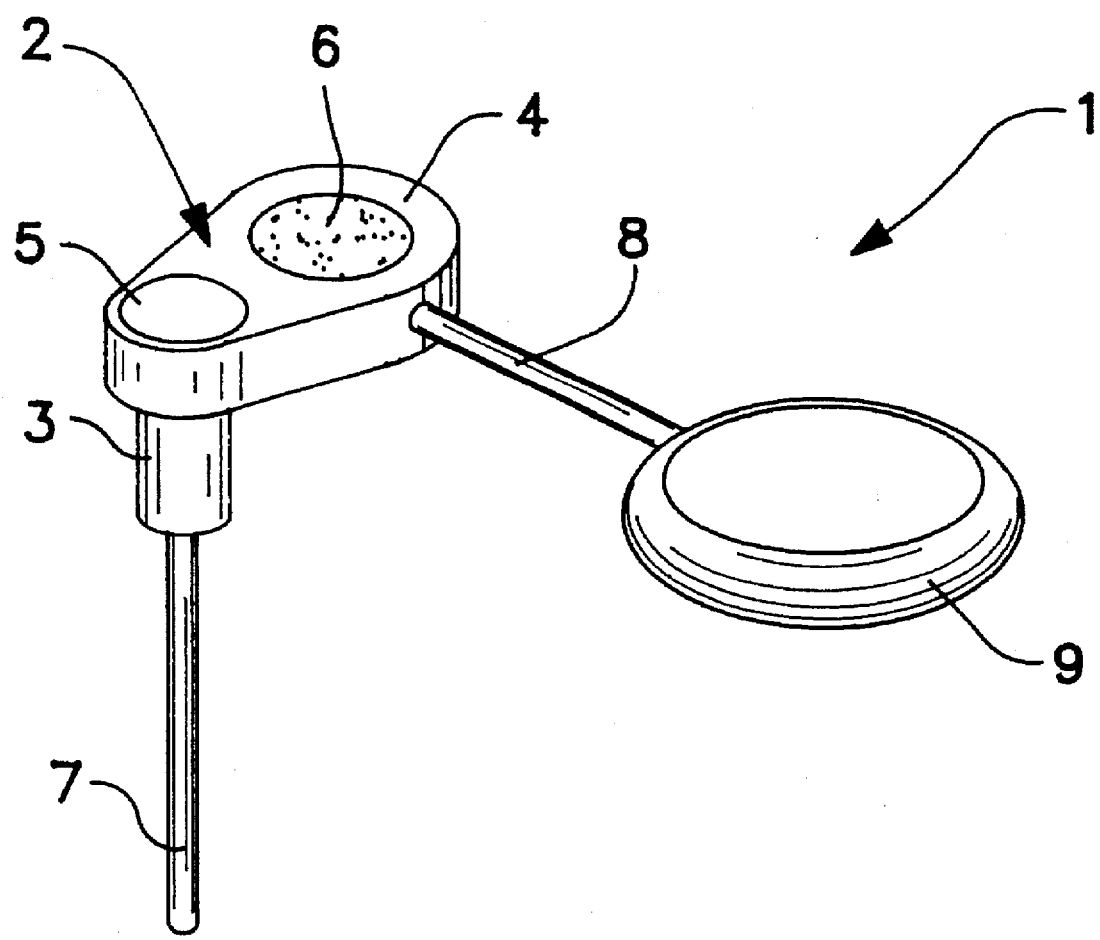

FIG. 5. The diagrammatic overall view of a third dosaging system according to the invention.

Figure 6:
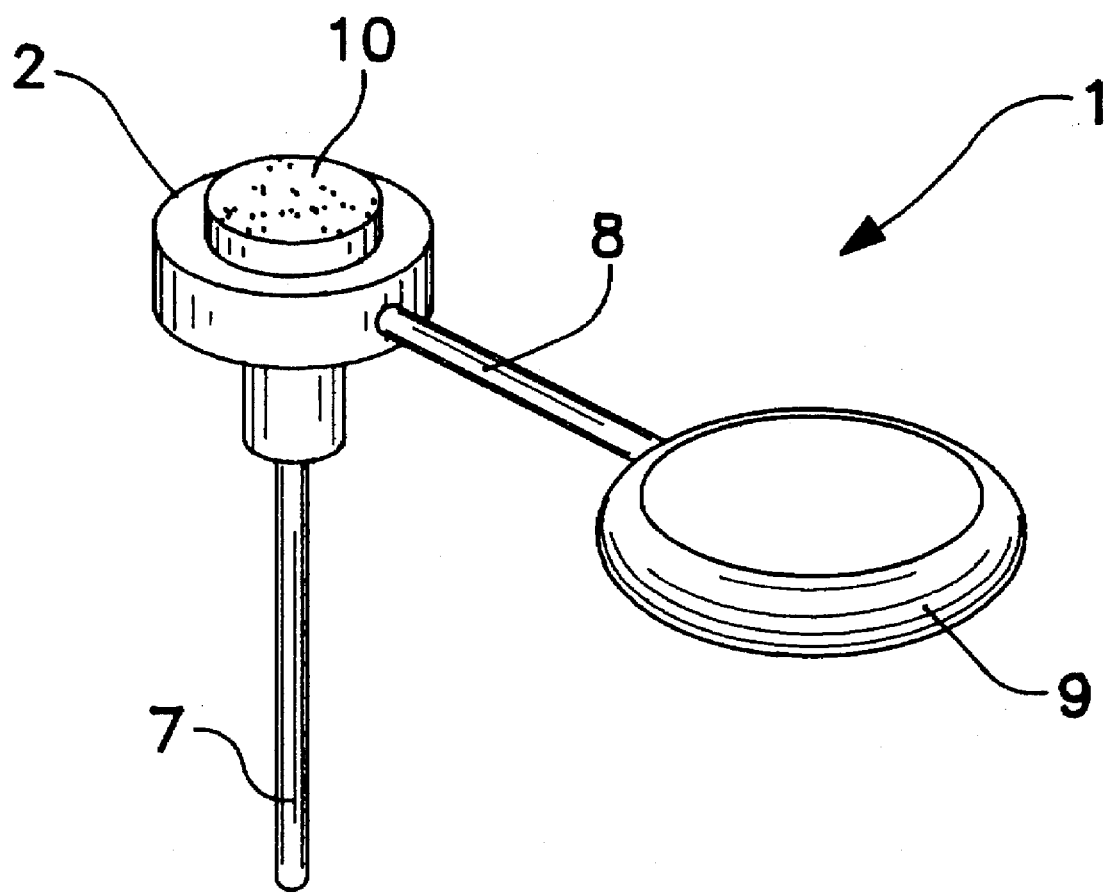

FIG. 6. The diagrammatic overall view of a fourth dosaging system according to the invention.

In the dosaging system 1 shown in FIG. 1 the housing 2 comprises a substantially cylindrical, first portion 3 and a second portion 4 directly adjacent to the first portion 3. Within the first portion 3 is provided a pump for the administration of the medication and which is not shown in FIG. 1. On the top of the housing 2 in the vicinity of the first portion 3 is provided an actuator 5 for pump actuation. In the vicinity of the second portion 4 on the top of the housing 2 there is a port 6, i.e. a self-sealing port, through which the medication reservoir formed within the housing 2 can be filled or emptied. On the side of the first portion 3 opposite to the actuator 5 is provided a discharge opening for the pump located in the interior of the housing 2 and which is not shown in FIG. 1. This discharge opening is connected to the dosaging line 7, whose free end can be located at the medication administration point.

The housing 2 shown in FIG. 1 can e.g. have a height of 1 to 2 cm (in the vertical direction on the first portion 3 corresponding to the position of the fitted pump) and a total length of 2 to 4 cm (on the top of the housing).

FIG. 2 diagrammatically shows a second embodiment of the dosaging system according to the invention. Despite the different construction compared with FIG. 1, for ease of viewing purposes, in FIG. 2 the same reference numerals as in FIG. 1 are used and this also applies to the subsequently described FIGS. 5 and 6.

In the case of the embodiment shown in FIG. 2, the dosaging system 1 substantially comprises two separate components, whereof one component corresponds to the first portion 3 and the second component to the second portion 4 in FIG. 1.

The first component contains in its interior a pump (not shown in FIG. 2) for administering the medication and has on its top an actuator 5. The second component forms a medication reservoir, on whose top is located a port 6. The first and second components are connected by means of a connecting line 8 for the transfer of the fluid from the medication reservoir into the pump. On the bottom of the first component having the pump is provided a dosaging or dosing line 7 for the transfer of the medication to the administration point.

The dimensions of the two components of the dosaging system 1 shown in FIG. 2 substantially correspond to the dimensions already given for the first portion 3 and second portion 4 of the dosaging system of FIG. 1.

FIG. 3 shows in a sectional view and in the implanted state an embodiment of the dosaging system according to the invention diagrammatically shown in FIG. 1, the pump being constituted by a piston pump.

The dosaging system 11 according to FIG. 3 is fixed in a corresponding recess of the bone 12, in this case the mastoid behind the ear muscle using a special cement 13. The necessary stepped drill cone in the mastoid is cut in the bone using a special microsurgical drilling technique.

The housing 14 of the dosaging system 11 is formed from a housing base part 15 and a housing lid 16. As a result of the indicated shape of the housing base part 15 and housing lid 16, the housing 14 forms a first portion 17 and a second portion 18. Within the first portion 17 is located a pump, which relative to the arrangement of the housing 14 in the non-implanted state is vertically fitted.

According to FIG. 3 the pump is constructed as a plunger pump 19 comprising the pump casing 20, in which is guided the plunger 21 with the aid of the sealing element 22. Through an axial displacement of the plunger 21 on operating the operating button 23 cooperating with the plunger, the fluid in the pump chamber 24 is transferred to the discharge chamber 25. The pipe compression valve blocking in the case of a vacuum in the pump chamber 24 is opened for introducing the fluid into the discharge chamber 25 as a result of the overpressure which occurs. In this way the fluid can flow to the administration point through the dosaging line 28 connected to the discharge opening 27 of the pump 19. After operating the operating button 23, the plunger 21 is returned by the restoring spring 29 to the initial state (non-initiated state). The plunger stroke is indicated by reference numeral 30 in FIG. 3. Below the casing lid 16 is provided a stop 31 for limiting the return movement of the plunger 21.

As can be seen in FIG. 3 most of the interior of the housing 14 serves as a medication reservoir 32. According to FIG. 3 there is fluid in the medication reservoir 32 up to the level 33. Above said level 33 there is a sterile gas cushion 34.

A pipe compression valve 35 is provided on the pump 19 as a suction valve for the fluid and blocks in the case of an overpressure in the pump chamber 24. In the case of a vacuum or underpressure said valve is opened and the fluid flows via the suction cannula 36 into the pump chamber 24.

Moreover, as an underpressure or vacuum valve for ventilation at least one further pipe compression valve 37 is provided on the pump 19, which opens and closes independently of the piston movement or the pressure ratios in the pump chamber 24. In the case of a sufficiently high vacuum in the medication reservoir 32 the pipe compression valve 37 opens automatically and thus permits the pressure compensation. The corresponding gas supply for the ventilation takes place by means of a suction duct 38, which is connectable by means of a ventilation catheter 47 e.g. to the middle ear cavity. In the second portion 18 of the housing 14 a puncture septum 39 is provided as the port and through it the medication reservoir 32 can be emptied, cleaned, disinfected, ventilated or filled. To facilitate the introduction of a cannula, a centring radius 40 is provided on the circumference of the puncture septum 39.

Finally, FIG. 3 also shows the elastic scalp 41, which following the implantation of the dosaging system 11 is again located at its original location above the operating point. To protect the tissue on the area of the scalp 41 where the operating button 23 for the pump 19 is located and below said scalp 41 is located an elastic membrane 42, which is higher than the housing lid 16 and is connected to the latter in its marginal area.

FIG. 4 shows another embodiment of the dosaging system according to the invention shown in FIG. 1 in the implanted state and in a sectional view. In this embodiment a diaphragm pump is used as a further miniaturizable pump principle.

As the dosaging system components according to FIG. 4 which do not apply to the pump are identical to the corresponding components of the embodiment of FIG. 3, reference can be made in this connection to the description of FIG. 3. Correspondingly, with regards to the same components in FIG. 4 the same reference numerals as in FIG. 3 are used.

In place of the plunger pump 19 in FIG. 3, FIG. 4 uses a so-called diaphragm pump 43, as is known from the prior art. In this pump 43 the connection between the actual pump body 44 and the actuator 45 is provided by a connecting line 46. On actuating the actuator 45 by means of the elastic membrane 42 shown in FIG. 3, the fluid located in the pump body is correspondingly brought via the discharge chamber 25 and with the aid of the discharge opening 27 and dosaging line 28 to the administration location. The pipe compression valves 35 and 37 ensure in the manner described in conjunction with FIG. 3 for the refilling of the diaphragm pump 43 or for the ventilation of the medication reservoir 32. FIG. 4 also shows a ventilation catheter 47 connected by means of the suction duct 38 with the hose valve 37.

In the actuator 45, according to FIG. 4 a restoring spring 48 is provided with the aid of which the elastic membrane 42 can be returned to its initial position after actuating the actuator 45. According to FIG. 4 there is also a stop 49, which prevents an excessive actuating stroke. As a function of the configuration of the dosaging system, said stop 49 may be superfluous. The broken line in FIG. 4 between the elastic membrane 42 and the stop 49 indicates said membrane 42 during its operation, i.e. the released state of the actuator 45.

FIGS. 5 and 6 show two further embodiments of the invention, where there is a separate medication reservoir, preferably made from elastic material.

The dosaging system 1 according to FIG. 5 comprises a housing 2 which, as in the embodiments described hereinbefore, preferably comprises a rigid, biocompatible material. In a cylindrical portion 3 of the housing 2 is housed a pump, not shown in FIG. 5, which can be operated with the aid of an operating button 5. On a flatter, further portion 4 of the housing 2 is provided a port (septum) 6. A dosaging line 7 leads from a discharge opening on the housing portion 3 not shown in FIG. 5 to the administration location. In addition, the dosaging system 1 according to FIG. 5 has a separate medication reservoir 9 made from an elastic, biocompatible material, particularly a plastics material. This medication reservoir 9 is connected to the housing 2, in the represented case the flatter housing portion 4, by means of a connecting line 8.

The dosaging system 1 according to FIG. 6 also comprises a preferably rigid housing 2, in whose interior is located a not shown pump. On the top of the housing 2 is provided an actuator 10, which not only serves to initiate the pump function but simultaneously constitutes the port (septum). This actuator 10 is raised compared with the top of the housing 2, so that it can be easily located both on initiating the pump function and also e.g. on refilling. A dosaging line 7 leads from the housing 2 to the administration location and the separate elastic medication reservoir 9 is connected by means of a connecting line 8 to the housing 2.

The embodiments of the invention described in FIGS. 5 and 6 have comparable dimensions to the previously described embodiments. In particular, the housing 2 is provided for implantation in the mastoid of the human. The pumping mechanisms described in FIGS. 3 and 4 can also be used in the embodiments according to FIGS. 5 and 6. The dosaging line/dosaging cannula is led from the discharge opening on the housing 2 into the middle ear and consequently allows a planned therapy of the middle or inner ear.

As a result of the elastic construction of the medication reservoir 9, no separate ventilating device is required for the microdosaging system according to the invention. As has already been described, the elastic medication reservoir (tank), can e.g. be implanted in the vicinity of the occiput, the neck or axilla beneath the skin.

We claim:

1. Implantable dosaging system for medications, active substances, etc., to be administered in the form of dissolved or suspended fluids, comprising:

a housing defining a medication reservoir, the housing having a self sealing injection port leading into the medication reservoir and a pump located within the housing for pumping a medication from the reservoir out of the housing through a discharge opening and a pump outlet for administering the medication, said pump being transcutaneously operable with the aid of an actuator located on the housing, a one way outlet valve being located at the pump outlet; and, wherein the pump is a piston plunger pump having a pump chamber coupled to the medication reservoir by an inlet check valve, the outlet valve is a fluid pressure-dependent opening pipe compression valve and the discharge opening can be reversibly supplied with fluid by the operation of the actuator of the pump via the pipe compression valve.

2. The dosaging system according to claim 1, wherein the housing is dimensionally stable and substantially rigid.

3. The dosaging system according to claim 1, wherein the housing is constructed of at least one of a biocompatible plastic and a biocompatible metal.

4. The dosaging system according to claim 1, wherein the housing is formed from a housing base part and a housing lid.

5. The dosaging system according to claim 1, wherein the shape of the housing is suitable for an implantation of the dosaging system in humans, in the bone region behind the ear muscle.

6. The dosaging system according to claim 1, wherein the medication reservoir is made from an elastic, biocompatible plastic material.

7. The dosaging system according to claim 1, wherein the medication reservoir is intended for implantation by fixing to the muscular fascia, e.g. in the vicinity of the axilla, neck or occiput.

8. The dosaging system according to claim 1, wherein the actuator is raised compared with the housing.

9. The dosaging system according to claim 1, wherein the actuator for the transcutaneous operation of the pump is formed by a pressure surface, which has a substantially elastic membrane.

10. The dosaging system according to claim 1, wherein the selfsealing port is formed by a puncture septum.

11. The dosaging system according to claim 1, wherein the actuator and self-sealing port are constructed as a unit and the pressure surface provided for transcutaneous operation is formed by a puncture septum.

12. The dosaging system according to claim 1, wherein the medication reservoir has a volume of approximately 1 to 5 $cm^3$.

13. The dosaging system according to claim 1, wherein the pump is constructed for the discontinuous administration of volumes between 10 to 20 µl.

14. The dosaging system according to claim 1, wherein the dosaging line is constructed for the administration of a therapeutic to the middle ear.

15. The dosaging system according to claim 1, wherein the dosaging line is constructed for the administration of a therapeutic to the inner ear.

16. The dosaging system according to claim 1, wherein the dosaging line has at the end associated with the administration point, a closure valve.

17. The dosaging system according to claim 1, further comprising a dosaging line leading from the discharge opening to an administration point.

18. Implantable dosaging system for medications, active substances, etc., to be administered in the form of dissolved or suspended fluids, comprising:

- a housing, said housing including a discharge opening for administering a medication;
- a medication reservoir located within said housing, said medication reservoir having a self sealing port for refilling;
- a plunger pump located within said housing, said plunger pump having a pump chamber, said plunger pump including an outlet and being transcutaneously operable with the aid of an actuator located on the housing;
- a first fluid pipe compression valve located between the pump chamber and the medication reservoir; and
- a second pipe compression valve located at the pump outlet;

wherein the discharge opening can be reversibly supplied with fluid by the operation of the actuator of the pump via the first and second pipe compression valves.

19. Dosaging system according to claim 18 further comprising:

- a suction duct extending from said medication reservoir through said housing; and
- a third pipe compression valve located between said suction duct and said medication reservoir for venting said medication reservoir.

* * * * *

UNITED STATES PATENT AND TRADEMARK OFFICE
CERTIFICATE OF CORRECTION

PATENT NO. : 5,895,372
DATED : April 20, 1999
INVENTOR(S) : Zenner, Hans Peter, et al.

It is certified that error appears in the above-identified patent and that said Letters Patent is hereby corrected as shown below:

<u>Column 9,</u>
Line 31, after "medication reservoir" insert --portion --.

<u>Column 10,</u>
Line 2, after "reservoir" insert -- portion --.
Line 38, (claim 6, line 2), after "medication reservoir" delete "is" and insert -- includes a portion --.
Line 40, (claim 7, line 1), delete "claim 1, wherein" and insert -- claim 6, wherein the portion of --.

Signed and Sealed this

Thirtieth Day of October, 2001

*Attest:*

NICHOLAS P. GODICI
*Attesting Officer*     *Acting Director of the United States Patent and Trademark Office*